United States Patent [19]

Barth

[11] 4,260,598

[45] Apr. 7, 1981

[54] METHOD FOR INCREASING ANTIBACTERIAL EFFECTIVENESS OF A β-LACTAM ANTIBIOTIC

[75] Inventor: Wayne E. Barth, East Lyme, Conn.

[73] Assignee: Pfizer Inc., New York, N.Y.

[21] Appl. No.: 87,250

[22] Filed: Oct. 22, 1979

Related U.S. Application Data

[63] Continuation-in-part of Ser. No. 950,971, Oct. 18, 1978, abandoned, which is a continuation-in-part of Ser. No. 863,799, Dec. 23, 1977, abandoned.

[51] Int. Cl.³ .............................................. A61K 31/43
[52] U.S. Cl. ...................................... 424/114; 424/271
[58] Field of Search ...................... 260/239.1, 249.2; 424/271, 114

[56] References Cited

U.S. PATENT DOCUMENTS

| | | | |
|---|---|---|---|
| 3,164,604 | 1/1965 | Doyle et al. | 260/306.7 C |
| 3,197,466 | 7/1965 | Chow et al. | 260/239.1 |
| 3,536,698 | 10/1970 | Chauvette et al. | 260/239.1 |
| 3,544,581 | 12/1970 | Essery | 260/306.7 C |
| 3,663,563 | 5/1972 | Fosker et al. | 260/306.7 C |
| 3,691,188 | 9/1972 | Spry | 260/306.7 |
| 3,994,912 | 11/1976 | Davis et al. | 260/306.7 C |
| 4,164,497 | 8/1979 | Kamiya et al. | 260/249.2 |
| 4,166,904 | 9/1979 | Hunt | 424/114 |
| 4,180,506 | 12/1979 | Pratt | 424/270 |

FOREIGN PATENT DOCUMENTS 2140119 2/1972 Fed. Rep. of Germany.
2824539 12/1978 Fed. Rep. of Germany.

OTHER PUBLICATIONS

C. Abstracts, vol. 76, P153735(n), (1972).
Abstracting, WGOLS 2,140,119.
Essery et al., J. Org. Chem., 30, 4388 (1965).
Guddal et al., Tetrahedron Letters, No. 9, 381 (1962).
Harrison et al., JCS, (London), Perkin I, 1972 (1976).
Chaikovskaya et al., Antibiotiki, 13, 155 (1968).
Cephalosporins & Penicillins, edited by E. Flynn, pp. 203–210 (1972), Academic Press.

*Primary Examiner*—Nicholas S. Rizzo
*Attorney, Agent, or Firm*—Connolly and Hutz

[57] ABSTRACT

6-Aminopenicillanic acid 1,1-dioxide, esters thereof readily hydrolyzable in vivo, and the pharmaceutically-acceptable salts of these compounds, are useful for enhancing the effectiveness of certain β-lactam antibiotics against certain β-lactamase producing bacteria. Derivatives of 6-aminopenicillanic acid 1,1-dioxide protected by a conventional carboxy protecting group are useful intermediates to 6-aminopenicillanic acid 1,1-dioxide and esters thereof readily hydrolyzable in vivo.

6 Claims, No Drawings

METHOD FOR INCREASING ANTIBACTERIAL EFFECTIVENESS OF A β-LACTAM ANTIBIOTIC

CROSS-REFERENCE TO RELATED APPLICATIONS

This application is a continuation-in-part of application Ser. No. 950,971, filed Oct. 18, 1978, now abandoned, which in turn is a continuation-in-part of application Ser. No. 863,799, filed Dec. 23, 1977, and now abandoned.

BACKGROUND OF THE INVENTION

One of the most well-known and widely used classes of antibacterial agents is the class known as the β-lactam antibiotics. These compounds are characterized in that they have a nucleus consisting of a 2-azetidinone (β-lactam) ring fused to either a thiazolidine or a dihydro-1,3-thiazine ring. When the nucleus contains a thiazolidine ring, the compounds are usually referred to generically as penicillins, whereas when the nucleus contains a dihydrothiazine ring, the compounds are referred to as cephalosporins. Typical examples of penicillins which are commonly used in clinical practice are benzylpenicillin (penicillin G), phenoxymethylpenicillin (penicillin V), ampicillin and carbenicillin; typical examples of common cephalosporins are cephalothin, cephalexin and cefazolin.

However, despite the wide use and wide acceptance of the β-lactam antibiotics as valuable chemotherapeutic agents, they suffer from the major drawback that certain members are not active against certain microorganisms. It is thought that in many instances this resistance of a particular microorganism to a given β-lactam antibiotic results because the microorganism produces a β-lactamse. The latter substances are enzymes which cleave the β-lactam ring of penicillins and cephalosporins to give products which are devoid of antibacterial activity. However, certain substances have the ability to inhibit β-lactamases, and when a β-lactamase inhibitor is used in combination with a penicillin or cephalosporin it can increase or enhance the antibacterial effectiveness of the penicillin or cephalosporin against certain microorganisms. It is considered that there is an enhancement of antibacterial effectiveness when the antibacterial activity of a combination of a β-lactamase inhibiting substance and a β-lactam antibiotic is significantly greater than the sum of the antibacterial activities of the individual components.

This invention relates to 6-aminopenicillanic acid 1,1-dioxide, a new β-lactamase inhibitor, esters thereof readily hydrolyzable in vivo, and salts of these compounds; and also derivatives of 6-aminopenicillanic acid 1,1-dioxide having a carboxy protecting group. Said latter compounds are useful as chemical intermediates for 6-aminopenicillanic acid 1,1-dioxide and esters thereof.

In Volume 76 (January to June 1972) of the Chemical Substances Index of Chemical Abstracts, there appears an entry under the heading "4-thia-1-aza-bicyclo[3.2.0]-heptane-2-carboxylic acid, 6-amino-3,3-dimethyl-7-oxo,4,4-dioxide." This latter name is, of course, an alternate name for 6-aminopenicillanic acid 1,1-dioxide. The Index refers to Abstract No. 153735n, which is an abstract of West German Offenlegungsschrift No. 2,140,119. However, Abstract No. 153735n makes no reference to any penicillin 1,1-dioxides. West German Offenlegungsschrift No. 2,140,119 discloses a new process for oxidizing penicillin derivatives (e.g. 6-aminopenicillanic acid) to the corresponding 1-oxide. It is stated that the latter process produces penicillin 1-oxides (e.g. 6-aminopenicillanic acid 1-oxide) uncontaminated by the corresponding 1,1-dioxides (e.g. 6-aminopenicillanic acid 1,1-dioxide). No other mention of penicillin 1,1-dioxides is made in West German Offenlegungsschrift No. 2,140,119.

1,1-Dioxides of benzylpenicillin, phenoxymethylpenicillin and certain esters thereof have been disclosed in U.S. Pat. Nos. 3,197,466 and 3,536,698, and in an article by Guddal et al., *Tetrahedron Letters*, No. 9, 381 (1962). Harrison et al., in the *Journal of the Chemical Society* (London), Perkin I, 1772 (1976), have disclosed a variety of penicillin 1,1-dioxides, including methyl phthalimidopenicillanate 1,1-dioxide and methyl 6,6-dibromopenicillanate 1,1-dioxide. U.S. Pat. No. 3,544,581 discloses 6-aminopenicillanic acid 1-oxide. Chaikovskaya et al., *Antibiotiki*, 13, 155 (1968), disclose that benzyl penicillin 1,1-dioxide was found to be inactive when tested for β-lactamase inhibiting activity against *E. coli*.

West German Offenlegungsschrift No. 2,824,535, published Dec. 14, 1978, and Iranian Pat. No. 19,601, granted July 12, 1978, disclose penicillanic acid 1,1-dioxide, and esters thereof readily hydrolyzable in vivo, as antibacterial agents and as β-lactamase inhibitors. Penicillanic acid 1,1-dioxide and esters thereof readily hydrolyzable in vivo increase the antibacterial effectiveness of certain penicillin and cephalosporin compounds against certain bacteria.

SUMMARY OF THE INVENTION

According to the invention there are provided novel compounds of the formula

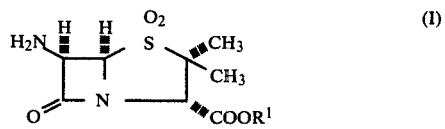

the pharmaceutically-acceptable acid-addition salts and the pharmaceutically-acceptable base salts thereof, wherein $R^1$ is selected from the group consisting of hydrogen, ester-forming residues readily hydrolyzable in vivo, and conventional penicillin carboxy protecting groups. The term "ester-forming residues readily hydrolyzable in vivo" is here intended to refer to non-toxic ester residues which are rapidly cleaved in mammalian blood or tissue, to release the corresponding free acid (i.e. the compound of formula I, wherein $R^1$ is hydrogen). Typical examples of such readily hydrolyzable ester-forming residues which can be used for $R^1$ are alkanoyloxymethyl having from 3 to 7 carbon atoms, 1-(alkanoyloxy)ethyl having from 4 to 8 carbon atoms, 1-methyl-1-(alkanoyloxy)ethyl having from 5 to 9 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, 3-phthalidyl, 4-crotonolactonyl and γ-butyrolacton-4-yl.

The compounds of the formula I, wherein $R^1$ is hydrogen or an ester-forming residue readily hydrolyzable in vivo, are useful for enhancing the antibacterial activity of β-lactam antibiotics. Said compounds of the formula I, wherein $R^1$ is a carboxy protecting group, are useful as chemical intermediates to the compound of the formula I, wherein $R^1$ is hydrogen, or an ester-forming residue readily hydrolyzable in vivo. A typical carboxy protecting group is benzyl.

Therefore, the β-lactamase inhibitors of this invention are the compounds of the formula

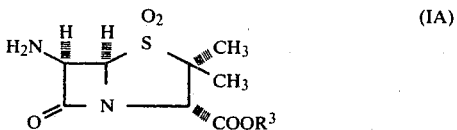

and the pharmaceutically-acceptable acid-addition salts and the pharmaceutically-acceptable base salts thereof, wherein $R^3$ is selected from the group consisting of hydrogen and ester-forming residues readily hydrolyzable in vivo.

Thus, also according to the invention, there is provided a method of increasing the antibacterial effectiveness of a β-lactam antibiotic in a mammalian subject, which comprises co-administering with said β-lactam antibiotic, to said mammalian subject, a β-lactam antibiotic effectiveness increasing amount of a compound of the formula IA, or a pharmaceutically-acceptable acid-addition salt thereof or a pharmaceutically-acceptable base salt thereof, wherein $R^3$ is selected from the group consisting of hydrogen and ester forming residues readily hydrolyzable in vivo.

DETAILED DESCRIPTION OF THE INVENTION

This invention relates to the novel compounds of formulas I and IA, and throughout this specification they are referred to as derivatives of penicillanic acid, which is represented by the structural formula

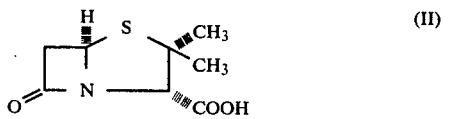

In formula II, broken line attachment of a substituent to the bicyclic nucleus indicates that the substituent is below the plane of the bicyclic nucleus. Such a substituent is said to be in the α-configuration. Conversely, solid line attachment of a substituent to the bicyclic nucleus indicates that the substituent is attached above the plane of the nucleus. This latter configuration is referred to as the β-configuration.

4-Crotonolactonyl and γ-butyrolacton-4-yl refer to structures III and IV, respectively. The wavy lines are intended to denote each of the two epimers and mixtures thereof.

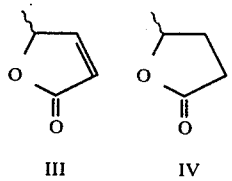

As indicated hereinbefore, the compounds of this invention are the compounds of formula I, and the pharmaceutically-acceptable acid-addition and base salts thereof. When $R^1$ is an ester-forming residue readily hydrolyzable in vivo in a compound of formula I, it is a grouping which is notionally derived from an alcohol of the formula $R^1$—OH, such that the moiety $COOR^1$ in such a compound of formula I represents an ester grouping. Moreover, $R^1$ is of such a nature that the grouping $COOR^1$ is readily cleaved in vivo to liberate a free carboxy group (COOH). That is to say, $R^1$ is a group of the type that when a compound of formula I, wherein $R^1$ is an ester-forming residue readily hydrolyzed in vivo, is exposed to mammalian blood or tissue, the compound of formula I, wherein $R^1$ is hydrogen, is readily produced. Such groups for $R^1$ are well-known in the penicillin art. In most instances the improve the absorption characteristics of the penicillin compound. Additionally, $R^1$ should be of such a nature that it imparts pharmaceutically-acceptable properties to a compound of formula I, and it liberates pharmaceutically-acceptable fragments when cleaved in vivo.

As indicated above, ester-forming residues readily hydrolyzable in vivo are well-known and are readily identified by those skilled in the penicillin art. See, for example, West German Offenlegungsschrift No. 2,517,316. Typical examples of such groups for $R^1$ are 3-phthalidyl, 4-crotonolactonyl, gamma-butyrolacton-4-yl and groups of the formula

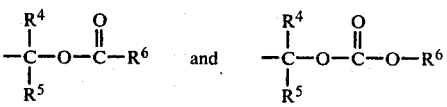

wherein $R^4$ and $R^5$ are each selected from the group consisting of hydrogen and alkyl having from 1 to 2 carbon atoms, and $R^6$ is alkyl having from 1 to 6 carbon atoms. However, preferred groups for $R^1$ are alkanoyloxymethyl having from 3 to 7 carbon atoms, 1-(alkanoyloxy)ethyl having from 4 to 8 carbon atoms, 1-methyl-1-(alkanoyloxy)ethyl having from 5 to 9 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, 3-phthalidyl, 4-crotonolactonyl and gamma-butyrolacton-4-yl.

Esters of 6-aminopenicillanic acid 1,1-dioxide readily hydrolyzable in vivo can also be termed bioprecursors of 6-aminopenicillanic acid 1,1-dioxide.

This invention relates to compounds of the formula I, wherein $R^1$ is hydrogen, an ester-forming residue readily hydrolyzable in vivo or a conventional carboxy protecting group. When it is a protecting group, $R^1$ is any carboxy protecting group conventionally used in the penicillin and/or cephalosporin art to protect the carboxy groups at the 3- and 4-positions respectively. The identity of the carboxy protecting group is not critical and typical examples which can be used are the tetrahydropyranyl group, the benzyl group, substituted benzyl groups (e.g. 4-nitrobenzyl), the benzylhydryl group, the 2,2,2-trichloroethyl group, the t-butyl group and the phenacyl group. See further: U.S. Pat. Nos. 3,632,850 and 3,197,466; British Patent No. 1,041,985, Woodward et al., *Journal of the American Chemical Society*, 88, 852 (1966); Chauvette, *Journal of Organic Chemistry*, 36, 1259 (1971); Sheehan et al., *Journal of Organic Chemistry*, 29, 2006 (1964); and "Cephalosporins and Penicillins, Chemistry and Biology", edited by H. E. Flynn, Academic Press, Inc., 1972.

In one method according to the invention, the compound of the formula I, wherein $R^1$ is hydrogen is obtained simply by removal of the protecting group from a compound of the formula I, wherein $R^1$ is a conventional carboxy protecting group. Naturally, the protecting group is removed in conventional manner for that specific group, although conditions must be chosen which are compatible with the β-lactam ring system. Conditions which are compatible with the β-lactam ring system are well-known to those skilled in the art.

Particularly useful protecting groups for $R^1$ are the benzyl group and substituted benzyl groups, especially 4-nitrobenzyl. Benzyl and substituted benzyl groups can be removed conveniently by catalytic hydrogenation. In this case, a solution in an inert solvent of the compound of the formula I, wherein $R^1$ is benzyl or substituted benzyl, is stirred or shaken under an atmosphere of hydrogen, or hydrogen mixed with an inert diluent such as nitrogen or argon, in the presence of a catalytic amount of a hydrogenation catalyst. Convenient solvents for this hydrogenation are lower-alkanols, such as methanol; ethers, such as tetrahydrofuran and dioxan; low molecular weight esters, such as ethyl acetate and butyl acetate; water; and mixtures of these solvents. However, it is usual to choose conditions under which the starting material is soluble. The hydrogenation is usually carried out at a temperature in the range from about 0° to about 60° C. and at a pressure in the range from about 1 to about 100 kg./cm.$^2$. The catalysts used in this hydrogenation reaction are the type of agents known in the art for this kind of transformation, and typical examples are the noble metals, such as nickel, palladium, platinum and rhodium. The catalyst is usually present in an amount from about 0.01 to about 2.5 weight-percent, and preferably from about 0.1 to about 1.0 weight-percent, based on the compound of formula I. It is often convenient to suspend the catalyst on an inert support; a particularly convenient catalyst is palladium suspended on an inert support such as carbon. Additionally it is usual to buffer the reaction mixture in order to operate at a pH in the range from about 4 to 9, and preferably from 6 to 8. Borate and phosphate buffers are commonly used. The reaction typically takes about one hour, after which the compound of the formula I, wherein $R^1$ is hydrogen, is recovered simply by filtration followed by removal of the solvent in vacuo.

A further particularly useful protecting group for $R^1$ is the 2,2,2-trichloroethyl group. This group can be removed by treating the compound of the formula I, wherein $R^1$ is 2,2,2-trichloroethyl, with zinc dust in acetic acid, formic acid or a phosphate buffer, according to well-known methods. See further: Woodward et al., *Journal of the American Chemical Society*, 88, 852 (1966); Pike et al., *Journal of Organic Chemistry*, 34, 3552 (1969); Just el al., *Synthesis*, 457 (1976).

The compound of the formula I, wherein $R^1$ is hydrogen can be purified, if desired, by methods well-known in the art, e.g. recrystallization or chromatography.

The compounds of the formula I, wherein $R^1$ is a carboxy protecting group can be prepared from a compound of the formula:

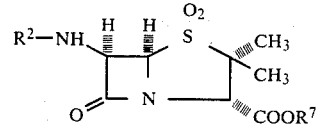

VII wherein $R^7$ is a conventional carboxy protecting group and $R^2$ is a conventional amino protecting group, by a process which simply involves removal of said amino protecting group. A variety of groups known in the art for protecing amino functions can be used for $R^2$. The major requirements for $R^2$ are that: (i) the group will reduce the nucleophilicity of the nitrogen atoms to which it is attached to such an extent that it is substantially unaffected during oxidation of the sulfide group in the thiazolidine ring to a sulfone grouping; and (ii) the protecting group $R^2$ can be removed under conditions which do not adversely affect the β-lactam ring of the compound of the formula I. Typical examples of amino protecting groups for $R^2$ are benzyloxycarbonyl and 2,2,2-trichloroethoxycarbonyl.

Removal of the protecting group $R^2$ from a compound of the formula VII, wherein $R^7$ is a conventional carboxy protecting group and $R^2$ is benzyloxycarbonyl, is readily accomplished by a conventional hydrogenation reaction. This can be carried out by the method described earlier for removal of the benzyl or substituted benzyl group from a compound of the formula I, wherein $R^1$ is benzyl or substituted benzyl. Moreover, removal of the trichloroethoxycarbonyl group from a compound of the formula VII, wherein $R^7$ is a conventional carboxy protecting group and $R^2$ is trichloroethoxycarbonyl, can be accomplished by zinc dust reduction. The conditions discussed earlier for removal of the trichloroethyl group from the compound of the formula I, wherein $R^1$ is trichloroethyl, can be used for this purpose.

As will be recognized by one skilled in the art, in the case wherein $R^7$ is benzyl or substituted benzyl, and $R^2$ is benzyloxycarbonyl, it is possible to remove $R^7$ and $R^2$ effectively in a single step by hydrogenation, to produce the compound of the formula I, wherein $R^1$ is hydrogen. Similarly, $R^7$ as trichloroethyl and $R^2$ as trichloroethoxycarbonyl can be removed effectively in a single step from a compound of formula VII by zinc dust reduction, to give the compound of formula I, wherein $R^1$ is hydrogen.

The compound of formula VII, wherein $R^7$ is a conventional carboxy protecting group and $R^2$ is a conventional amino protecting group, can be prepared from the corresponding compound of the formula

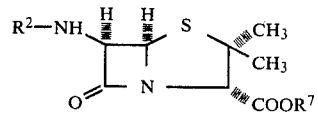

VIII by oxidation. A wide variety of oxidants known in the art for the oxidation of sulfides to sulfones can be used for this process. However, particularly convenient reagents are alkali metal permanganates, e.g. potassium permanganate, and organic peracids, e.g. 3-chloroperbenzoic acid. The latter named reagent is a particularly convenient oxidant.

When a compound of the formula VIII, wherein $R^7$ and $R^2$ are as previously defined, is oxidized to the corresponding compound of the formula VII, using 3-chloroperbenzoic acid, the reaction is usually carried out by treating the compound of the formula VIII with from about 2 to 4 molar equivalents, and preferably about 2.2 equivalents, of the oxidant in a reaction-inert organic solvent. Typical solvents are chlorinated hydrocarbons, such as dichloromethane, chloroform and 1,2 dichloroethane and ethers such as diethyl ether, tetrahydrofuran and 1,2-dimethoxyethane. The reaction is normally carried out at a temperature of from about 0° to about 80° C., and preferably at about 25° C. At about 25° C. reaction times of about 2 to about 16 hours are commonly used. The product is normally isolated by removal of the solvent by evaporation in vacuo. The product can be purified by conventional methods, well-known in the art.

The compounds of the formula VIII are either known compounds, which are prepared by published procedures, or they are analogs of known compounds, which are prepared by analogous procedures. In general the compounds of the formula VIII are prepared simply by attaching the protecting groups $R^7$ and $R^2$ to the well-known intermediate 6-aminopenicillanic acid. The groups $R^7$ and $R^2$ can be attached by the known method for the particular group, taking due account of the stability of the β-lactam ring system. In many instances the order of attachment of $R^7$ and $R^2$ is not critical.

The compounds of formula I, wherein $R^1$ is hydrogen, can be prepared by removal of the protecting group $R^2$ from a compound of the formula

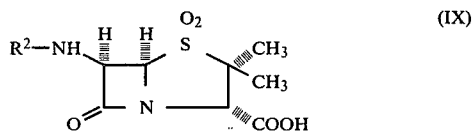

wherein $R^2$ is a conventional amino protecting group. The group $R^2$ is removed in the same manner as that described earlier for removal of $R^2$ from a compound of formula VII.

The compounds of formula IX, wherein $R^2$ is a conventional amino protecting group, can be prepared by oxidation of a compound of the formula

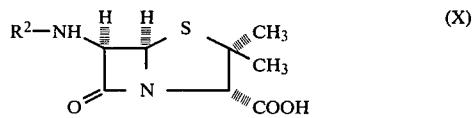

wherein $R^2$ is a conventional amino protecting group. This oxidation is carried out in exactly the same manner as described previously for oxidation of a compound of the formula VIII to VII.

The compounds of formula X are prepared from 6-aminopenicillanic acid by attachment of the protecting group thereto. The protecting group is attached in conventional manner, having due regard for the lability of the β-lactam ring system.

Compounds of the formula I, wherein $R^1$ is an ester-forming residue readily hydrolyzable in vivo, can be prepared from a compound of the formula X, wherein $R^2$ is a conventional amino protecting group, by a three-step sequence which comprises: (a) esterification of said compound of formula X, to give a compound of formula

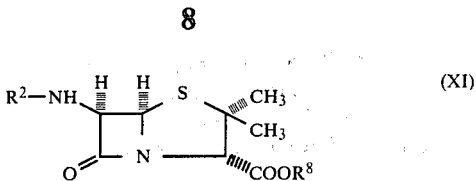

wherein $R^2$ is as defined previously and $R^8$ is an ester-forming residue readily hydrolyzed in vivo; (b) oxidation of the compound of formula XI, to give a compound of formula

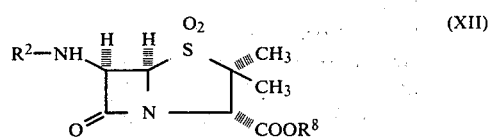

wherein $R^2$ and $R^8$ are as defined previously; and (c) removal of the protecting group $R^2$.

Step (a) of the above sequence is carried out in a manner which is determined by the precise structure of the ester-forming residue, but an appropriate method will be readily selected by one skilled in the art. In the case wherein $R^1$ is selected from the group consisting of 3-phthalidyl, 4-crotonolactonyl, gamma-butyrolacton-4-yl and groups of the formula V and VI, wherein $R^4$, $R^5$ and $R^6$ are as defined previously, a convenient method comprises alkylation of the compound of formula X with a 3-phthalidyl halide, a 4-crotonolactonyl halide, a gamma-butyrolacton-4-yl halide or a compound of the formula

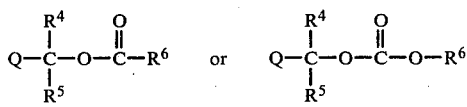

wherein Q is halo, and $R^4$, $R^5$ and $R^6$ are as previously defined. The terms "halide" and "halo" are intended to means derivatives of chlorine, bromine and iodine. The reaction is conveniently carried out by dissolving a salt of said compound of formula X in a suitable, polar, organic solvent, such as N,N-dimethylformamide, and then adding about one molar equivalent of the halide. When the reaction has proceeded essentially to completion, the product is isolated by standard techniques. It is often sufficient simply to dilute the reaction medium with an excess of water, and then extract the product into a water-immiscible organic solvent and then recover same by solvent evaporation. Salts of the compound of formula X which are commonly used are alkali metal salts, such as sodium and potassium salt, and tertiary amine salts, such as triethylamine, ethyldiisopropylamine, N-ethylpiperidine, N,N-dimethylaniline and N-methylmorpholine salts. The reaction is run at a temperature in the range from about 0° to 100° C., and usually at about 25° C. The length of time needed to reach completion varies according to a variety of factors, such as the concentration of the reactants and the reactivity of the reagents. Thus, when considering the halo compound, the iodide reacts faster than the bromide, which in turn reacts faster than the chloride. In fact, it is sometimes advantageous, when utilizing a chloro compound, to add up to one molar equivalent of an alkali metal iodide. This has the effect of speeding up the reaction. With full regard for the foregoing factors, reaction times of from about 1 to about 24 hours are commonly used. Step (b) of the above sequence involves oxidation of compound XI to compound XII. This reaction is carried out in the same manner as that described earlier for the oxidation of compound VIII to compound VII.

Step (c) of the above sequence involves removal of the protecting group $R^2$. Said protecting group $R^2$ is removed in conventional manner. For example, benzyl and substituted benzyl groups can be removed by catalytic hydrogenation, using the method described earlier for removal of such groups from a compound of formula I, wherein $R^1$ is benzyl or substituted benzyl, to give the compound of formula I, wherein $R^1$ is hydrogen.

The compound of formula I, wherein $R^1$ is hydrogen, is acidic and will form salts with basic agents. Such salts are considered to be within the scope of this invention. These salts can be prepared by standard techniques, such as contacting the acidic and basic components, usually in a stoichiometric ratio, in an aqueous, non-aqueous or partially aqueous medium, as appropriate. They are then recovered by filtration, by precipitation with a non-solvent followed by filtration, by evaporation of the solvent, or in the case of aqueous solutions, by lyophilization, as appropriate. Basic agents which are suitably employed in salt formation belong to both the organic and inorganic types, and they include ammonia, organic amines, alkali metal hydroxides, carbonates, bicaronates, hydrides and alkoxides, as well as alkaline earth metal hydroxides, carbonates, hydrides and alkoxides. Representative examples of such bases are primary amines, such as n-propylamine, n-butylamine, cyclohexylamine, benzylamine, and octylamine; secondary amines, such as diethylamine, morpholine, pyrrolidine and piperidine; tertiary amines, such as triethylamine, N-ethylpiperidine, N-methylmorpholine and 1,5-diazabicyclo[4.3.0]non-5-ene; hydroxides, such as sodium hydroxide, potassium hydroxide, ammonium hydroxide and barium hydroxide; alkoxides, such as sodium ethoxide and potassium ethoxide; hydrides, such as calcium hydride and sodium hydride; carbonates, such as potassium carbonate and sodium carbonate; bicarbonates, such as sodium bicarbonate and potassium bicarbonate; and alkali metal salts of long-chain fatty acids, such as sodium 2-ethylhexanoate.

Preferred base salts of the compound of the formula I, wherein $R^1$ is hydrogen, are sodium, potassium and triethylamine salts.

The compounds of formula I are basic, and they will form acid-addition salts. Such salts are within the scope of this invention, and they are prepared by standard techniques for penam compounds. Examples of acid-addition salts which are particularly valuable are hydrochloride, hydrobromide, phosphate, perchlorate, citrate, tartrate, pamoate, glutarate and 4-toluenesulfonate salts.

As indicated hereinbefore, the compounds of the formula IA, and pharmaceutically-acceptable salts thereof, are inhibitors of microbial β-lactamases, and they increase the antibacterial effectiveness of β-lactam antibiotics (penicillins and cephalosporins) against many microorganisms which produce a β-lactamase. The manner in which the compound of the formula IA, wherein $R^3$ is hydrogen, increases the effectiveness of a β-lactam antibiotic in vitro can be appreciated by reference to experiments in which the MIC (Minimum Inhibitory Concentration) of a given antibiotic alone, and said compound of the formula IA alone, are measured. These MIC's are then compared with the MIC values obtained with a combination of the given antibiotic and said compound of the formula IA. When the antibacterial potency of the combination is significantly greater than would have been predicted from the potencies of the individual compounds, this is considered to constitute enhancement of activity. The MIC values of combinations are measured using the method described by Barry and Sabath in "Manual of Clinical Microbiology", edited by Lenette, Spaulding and Truant, 2nd edition, 1974, American Society for Microbiology.

Typical examples of β-lactam antiobiotics with which a compound of IA, or salt or ester thereof readily hydrolyzable in vivo, can be co-administered are
6-(2-phenylacetamido)penicillanic acid,
6-(2-phenoxyacetamido)penicillanic acid,
6-(2-phenylpropionamido)penicillanic acid,
6-(D-2-amino-2-phenylacetamido)penicillanic acid,
6-(D-2-amino-2-[4-hydroxyphenyl]acetamido)penicillanic acid,
6-(D-2-[4-ethylpiperazin-2,3-dione-1-carboxamido]-2-phenylacetamido)penicillanic acid,
6-(D-2-[4-hydroxy-1,5-naphthyridine-3-carboxamido]-2-phenylacetamido)penicillanic acid,
6-(D-2-[imidazolidin-2-one-1-carboxamido]-2-phenylacetamido)penicillanic acid,
6-(D-[3-methylsulfonylimidazolidin-2-one-1-carboxamido]-2-phenylacetamido)penicillanic acid,
6-(D-2-[3-furfurylidineamino-2-oxoimidazolidine-1-carboxamido]-2-[4-hydroxyphenyl]acetamido)penicillanic acid,
7-(D-2-formyloxy-2-phenylacetamido)-3-([1-methyl-5-tetrazolyl]thiomethyl)-3-desacetoxymethylcephalosporanic acid,
7-(D-2-amino-2-[4-hydroxyphenyl]acetamido)-desacetoxycephalosporanic acid,
7-(2-[2-thienyl]acetamido)cephalosporanic acid,
7-(2-[1-tetrazolyl]acetamido-3-([5-methyl-1,3,4-thiadiazoly-2-yl]thiomethyl)-3-desacetoxymethylcephalosporanic acid,
7-(D-2-amino-2-phenylacetamido)desacetoxycephalosporanic acid,
7-(D-2-hydroxy-2-phenylacetamido)-3-([1-methyl-5-tetrazolyl]thiomethyl)-3-desacetoxymethylcephalosporanic acid,
7-(2-[4-pyridylthio]acetamido)cephalosporanic acid,
7-(D-2-amino-2-[1,4-cyclohexadienyl]acetamido)cephalosporanic acid,
7-(D-2-[4-ethylpiperazin-2,3-dione-1-carboxamido]-2-[4-hydroxyphenyl]acetamido)-3-([1-methyl-5-tetrazolyl]thiomethyl)-3-desacetoxymethylcephalosporanic acid
and the pharmaceutically-acceptable salts thereof.

In particular, 6-aminopenicillanic acid 1,1-dioxide, esters thereof readily hydrolyzable in vivo and pharmaceutically-acceptable salts thereof enhance the antibacterial effectiveness of penicillin G against anerobic bacteria, such as Bacteroides spp., and the effectiveness of ampicillin against resistant strains of *Staphylococcus aureus*.

The ability of the compounds of the formula IA, wherein $R^3$ is selected from the group consisting of hydrogen and ester-forming residues readily hydrolyzable in vivo, and salts thereof, to enhance the effectiveness of a β-lactam antibiotic against certain β-lactamase-producing bacterial makes them valuable for co-administration with certain β-lactam antibiotics in the treatment of bacterial infections in mammals particularly man. In the treatment of a bacterial infection, a compound of formula IA can be comingled with the β-lactam antibiotic, and the two agents thereby administered simultaneously. Alternatively, a compound of formula IA can be administered as a separate agent during a course of treatment with a β-lactam antibiotic.

When using a compound of formula IA, or salt thereof, antibacterial activity of a β-lactam antibiotic, the compound of formula IA, or salt thereof, can be administered alone, or preferably, in formulations with standard pharmaceutical carriers and diluents. The compound of formula IA, wherein $R^3$ is hydrogen, and the pharmaceutically-acceptable salts thereof, can be administered parenterally; the compounds of formula IA, wherein $R^3$ is an ester-forming residue readily hydrolyzable in vivo, and the pharmaceutically-acceptable salts thereof, can be administered both orally and parenterally. Parenteral administration includes intramuscular, subcutaneous, intraperitoneal and intravenous administration.

When a compound of formula IA is used in the presence of a carrier or diluent, said carrier or diluent is chosen on the basis of the intended mode of administration. For example, when considering the oral mode of administration, the compound of formula IA, or salt thereof, can be used in the form of tablets, capsules, lozenges, troches, powders, syrups, elixirs, aqueous solutions and suspensions, and the like, in accordance with standard pharmaceutical practice. The proportional ratio of active ingredients to carrier will naturally depend on the chemical nature, solubility, stability and potency of the active ingredients, as well as the dosage comtemplated. However, these pharmaceutical compositions will likely contain from about 5% to about 80% of carrier. In the case of tablets for oral use, carriers which are commonly used include lactose, sodium citrate and salts of phosphoric acid. Various disintegrants such as starch, and lubricating agents, such as magnesium stearate, sodium lauryl sulfate and talc, are commonly used in tablets. For oral administration in capsule form, useful diluents are lactose and high molecular weight polyethylene glycols. When aqueous suspensions are required for oral use, the active ingredients are combined with emulsifying and suspending agents. If desired, certain sweetening and/or flavoring agents can be added. For parenteral administration, which includes intramuscular, intraperitoneal, subcutaneous and intravenous use, sterile solutions of the active ingredients are usually prepared, and the pH or the solutions are suitably adjusted and buffered. For intravenous use, the total concentration of solutes should be controlled to render the preparation isotonic.

Although the prescribing physician will ultimately decide the dosage to be used in a human subject, the ratio of the daily dosages of a compound of formula IA, or salt thereof, and the β-lactam antibiotic will normally be in the range from about 1:3 to 3:1. Additionally, the daily oral dosage of each component will normally be in the range from about 10 to about 200 mg. per kilogram of body weight and the daily parenteral dosage of each component will normally be about 10 to about 400 mg. per kilogram of body weight. These figures are illustrative only, however, and in some cases it may be necessary to use dosages outside these limits.

The following examples are provided solely for the purpose of further illustration. Infrared (IR) spectra were measured as potassium bromide discs (KBr discs), and diagnostic absorption bands are reported in wave numbers (cm$^{-1}$). Nuclear magnetic resonance spectra (NMR) were measured at 60 MHz for solutions in deuterochloroform (CDCl$_3$) or deuterium oxide (D$_2$O), and peak positions are expressed in parts per million (ppm) downfield from tetramethylsilane or sodium 2,2-dimethyl-2-silapentane-5-sulfonate. The following abbreviations for peak shapes are used: s, singlet; d, doublet; t, triplet; q, quartet; m, multiplet.

EXAMPLE 1

Sodium 6-Aminopenicillanate 1,1-Dioxide

To a slurry of 4.7 g. of 5 percent palladium-on-carbon in 10 ml. of water was added a solution of 4.7 g. of benzyl 6-benzyloxycarbonylaminopenicillanate 1,1-dioxide in 50 ml. of ethyl acetate. The mixture was hydrogenated at a pressure from 58-44 p.s.i.g. for 15 minutes. To the mixture was then added 2.5 ml. of 2 N sodium hydroxide, and the resulting mixture was filtered. The aqueous phase was removed, its pH was adjusted to 5.3, and then it was freeze-dried. This afforded 1.19 g. of the title product. The IR spectrum (KBr disc) showed absorptions at 1810, 1610, 1320 and 1120 cm$^{-1}$. The NMR spectrum (in D$_2$O) showed absorptions at 5.01 (d, 1H, J=4 Hz), 4.87 (d, 1H, J=4 Hz), 4.24 (s, 1H), 1.55 (s, 3H) and 1,.42 (s, 3H), ppm.

EXAMPLE 2

6-Aminopenicillanic Acid 1,1-Dioxide

To a solution of 2.70 g. (0.01 mole) of sodium 6-aminopenicillanate 1,1-dioxide in 30 ml. of water is added 5 ml. of 2 N hydrochloric acid. The mixture is concentrated to small volume in vacuo, and then the solid which precipitates is collected by filtration. This affords the title zwitterion.

EXAMPLE 3

Benzyl 6-Aminopenicillanate 1,1-Dioxide

To 1.23 g. (2.4 mmole) of benzyl 6-(2,2,2-trichloroethoxycarbonylamino)penicillanate 1,1-dioxide in 20 ml. of tetrahydroduran is added 2.0 g. of zinc dust followed by 4.0 ml. of 1 M potassium dihydrogen phosphate, with vigorous stirring. Stirring is continued for 1 hour, and then a further 2.0 g. of zinc dust and 4.0 ml. of 1 M potassium dihydrogen phosphate are added. After an additional 1 hour of stirring the reaction mixture is filtered, and the filtrate is evaporated in vacuo, maintaining the pH in the range 6.5 to 7.0. The aqueous residue is diluted with a further quantity of water, and then the product is extracted with ethyl acetate. The ethyl acetate is washed with water, and then dried using sodium sulfate. Evaporation of the dried ethyl acetate solution in vacuo affords the title compound.

EXAMPLE 4

6-Aminopenicillanic Acid 1,1-Dioxide

Hydrogenation of the benzyl ester of 6-aminopenicillanic acid 1,1-dioxide using the procedure of Example 1 affords 6-aminopenicillanic acid 1,1-dioxide, as its sodium salt. The sodium salt can be converted to the corresponding zwitterion using the procedure of Example 2.

EXAMPLE 5

Benzyl 6-Aminopenicillanate 1,1-Dioxide Hydrochloride

To a solution of 3.06 g. (0.01 mole) of benzyl 6-aminopenicillanate 1,1-dioxide in 30 ml. of methanol is added 20 ml. of 0.5 N methanolic hydrogen chloride. The solvent is then removed by evaporation in vacuo to give the title salt.

EXAMPLE 6

Pivaloyloxymethyl 6-Aminopenicillanate 1,1-Dioxide

To a slurry of 2.0 g. of 5% palladium-on-carbon in 20 ml. of ethyl acetate is added a solution of 2.0 g. of pivaloyloxymethyl 6-benzyloxycarbonylaminopenicillanate 1,1-dioxide in 10 ml. of ethyl acetate. The mixture is shaken under an atmosphere of hydrogen at a pressure of ca 50 psig for 30 minutes. The mixture is filtered, and the solvent is removed by evaporation in vacuo to give the title compound.

The product is redissolved in a small volume of ethyl acetate and a 0.5 M solution of 4-toluenesulfonic acid is added dropwise slowly. This causes the 4-toluenesulfonate salt of the title compound to precipitate. It is recovered by filtration.

EXAMPLE 7

Removal of the benzyloxycarbonyl group from each of the 6-benzyloxycarbonylaminopenicillanic acid esters of Preparation 7 by hydrogenolysis, using the procedure of Example 6, affords:
3-phthalidyl 6-aminopenicillanate 1,1 dioxide,
4-crotonolactonyl 6-aminopenicillanate 1,1-dioxide,
γ-butyrolacton-4-yl 6-aminopenicillanate 1,1-dioxide,
acetoxymethyl 6-aminopenicillanate 1,1-dioxide,
hexanoyloxymethyl 6-aminopenicillanate 1,1-dioxide,
1-(acetoxy)ethyl 6-aminopenicillanate 1,1-dioxide,
1-(isobutyryloxy)ethyl 6-aminopenicillanate 1,1-dioxide,
1-methyl-1-(acetoxy)ethyl 6-aminopenicillanate 1,1-dioxide,
1-methyl-1-(hexanoyloxy)ethyl 6-aminopenicillanate (1,1-dioxide,
methoxycarbonyloxymethyl 6-aminopenicillanate 1,1-dioxide,
propoxycarbonyloxymethyl 6-aminopenicillanate 1,1-dioxide,
1-(ethoxycarbonyloxy)ethyl 6-aminopenicillanate 1,1-dioxide,
1-(butoxycarbonyloxy)ethyl 6-aminopenicillanate 1,1-dioxide,
1-methyl-1-(methoxycarbonyloxy)ethyl 6-aminopenicillanate 1,1-dioxide,
1-methyl-1-(isopropoxycarbonyloxy)ethyl 6-aminopenicillanate 1,1-dioxide,
respectively.

PREPARATION 1

6-Benzyloxycarbonylaminopenicillanic Acid

To a suspension of 108 g. of 6-aminopenicillanic acid in 200 ml. of water was added a small amount of ice. The suspension was stirred mechanically in an ice bath, while the pH was adjusted to 7.3 using 6 N sodium hydroxide. To the mixture thus obtained was added 200 ml. of acetone plus a small amount of additional ice. This was followed by the addition of 86 ml. of benzyl chloroformate in acetone in two portions approximately five minutes apart. The pH was maintained in the range of 6.5-7.0 by addition of further 6 N sodium hydroxide. The mixture was stirred for approximately 45 minutes and then the pH was adjusted to 7.0. The reaction mixture was washed twice with ethyl acetate, and then further fresh ethyl acetate was added to the aqueous phase. The pH was adjusted to 2.7 and the layers were separated. The ethyl acetate layer was washed with sodium chloride solution, dried using anhydrous sodium sulfate and evaporated in vacuo. This afforded 188 g. of the title product, contaminated with a small amount of solvent. The NMR spectrum of the product (in $CDCl_3$) showed absorptions at 7.32 (s), 6.05-5.26 (m), 5.08 (s), 4.41 (s), 1.63 (s) and 1.54 (s) ppm.

PREPARATION 2

Benzyl 6-benzyloxycarbonylaminopenicillanate

To a solution of 188 g. of 6-benzyloxycarbonylaminopenicillanic acid (from Preparation 1) in 300 ml. of N,N-dimethylformamide was added 82.7 ml. of diisopropylethylamine. This caused a solid to precipitate, and an additional 100 ml. of N,N-dimethylformamide was added. To this mixture was then added 57 ml. of benzyl bromide and the resulting mixture was stirred overnight at room temperature under nitrogen. The solids which were then present were removed by filtration and discarded. The filtrate was divided in half and each half was combined with 600 ml. of water and 500 ml. of ethyl acetate. The pH was adjusted to 3.0, and the ethyl acetate layers were removed and combined. The combined ethyl acetate solution was washed with 500 ml. of water at pH 2.9. The ethyl acetate solution was then twice washed with 400 ml. of water adjusted to pH 8.1. Finally, the ethyl acetate solution was washed with 400 ml. of sodium chloride solution and dried using anhydrous sodium sulfate. Evaporation of the dried solution in vacuo afforded 230.7 g. of the title compound as an amber oil. The NMR spectrum of the product (in $CDCl_3$) showed absorptions at 7.29 (s, 10H), 5.88-5.25 (m, 2H), 5.08 (s, 2H), 4.43 (s, 1H), 1.57 (s, 3H) and 1.38 (s, 3H) ppm.

PREPARATION 3

Benzyl 6-Benzyloxycarbonylaminopenicillanate 1,1-Dioxide

To a solution of 217.8 g. of benzyl 6-benzyloxycarbonylaminopenicillanate in 450 ml. of methylene chloride was added 250 g. of m-chloroperbenzoic acid with stirring, over a period of one hour. The reaction mixture was allowed to warm to room temperature and stirring was continued overnight. At this point the solid material was removed by filtration and discarded, and the filtrate was evaporated to dryness in vacuo. The resulting solid was partitioned between 500 ml. of ethyl acetate and 500 ml. of water and the pH was adjusted to 7.4 using saturated sodium bicarbonate solution. The ethyl acetate layer was removed and added to 400 ml. of water and the pH was adjusted to 8.2 with saturated sodium bicarbonate solution. This resulted in the formation of an emulsion, which was divided into two equal portions. To each portion was added 200 ml. of saturated sodium chloride solution and 200 ml. of ethyl acetate. This caused the emulsion to break up and the ethyl acetate layers were removed and combined. The resulting combined ethyl acetate solution was washed with 200 ml. of sodium chloride solution and dried over anhydrous sodium sulfate. Evaporation of the dry ethyl acetate solution in vacuo afforded 168 g. of crude product. This crude product was slurried with methanol and the solid material was removed by filtration. This afforded 70 g. of the title product in substantially pure form. The methanol mother liquors were evaporated to dryness and a small amount of methanol was added to the residue. This mixture was refrigerated, which caused a further amount of solid to appear. This solid was collected by filtration, affording a further 7 g. of the title compound in substantially pure form.

The NMR spectrum (in CDCl$_3$) showed absorption at 7.29 (s, 10H), 6.22 (d, 1H, J=10 Hz), 5.77 (dd, 1H, J=4 Hz, J$_2$=10 Hz), 5.20–5.05 (m, 4H), 4.70 (d, 1H, J=4 Hz), 4.48 (s, 1H), 1.49 (s, 3H), and 1.24 (s, 3H) ppm.

PREPARATION 4

Pivaloyloxymethyl 6-Benzyloxycarbonylaminopenicillanate

To a stirred solution of 3.50 g. of 6-benzyloxycarbonylaminopenicillanic acid in 15 ml. of N,N-dimethylformamide is added 1.30 g of diisopropylethylamine followed by 1.55 g. of chloromethyl pivalate and 50 mg. of sodium iodide at ca. 0° C. The reaction mixture is stirred at ca. 0° C. for 30 minutes and then at room temperature for 24 hours. The reaction mixture is then diluted with ethyl acetate and water and the pH of the aqueous phase is adjusted to 7.5. The ethyl acetate layer is separated and washed three times with water and once with saturated sodium chloride solution. The ethyl acetate solution is then dried using anhydrous sodium sulfate, and evaporated in vacuo to give the title compound.

PREPARATION 5

Reaction of 6-benzyloxycarbonylaminopenicillanic acid with 3-phthalidyl chloride, 4-crotonolactonyl chloride, gamma-butyrolacton-4-yl chloride or the requisite alkanoyloxymethyl chloride, 1-(alkanoyloxy)-ethyl chloride, 1-methyl-1-(alkanoyloxy)ethyl chloride, alkoxycarbonyloxymethyl chloride, 1-(alkoxycarbonyloxy)-ethyl chloride or 1-methyl-1-(alkoxycarbonyloxy)ethyl chloride, according to the procedure of Preparation 4, affords the following compounds:
3-phthalidyl 6-benzyloxycarbonylaminopenicillanate,
4-crotonolactonyl 6-benzyloxycarbonylaminopenicillanate,
γ-butryolaction-4-yl 6-benzyloxycarbonylaminopenicillanate,
acetoxymethyl 6-benzyloxycarbonylaminopenicillanate,
hexanoyloxymethyl 6-benzyloxycarbonylaminopenicillanate,
1-(acetoxy)ethyl 6-benzyloxycarbonylaminopenicillanate,
1-(isobutyryloxy)ethyl 6-benzyloxycarbonylaminopenicilanate,
1-methyl-1-(acetoxy)ethyl 6-benzyloxycarbonylaminopenicillanate,
1-methyl-1-(hexanoyloxy)ethyl 6-benzyloxycarbonylaminopenicillanate,
methoxycarbonyloxymethyl 6-benzyloxycarbonylaminopenicillanate,
propoxycarbonyloxymethyl 6-benzyloxycarbonylaminopenicillanate,
1-(ethyloxycarbonyloxy)ethyl 6-benzyloxycarbonylaminopenicillanate,
1-(butoxycarbonyloxy)ethyl 6-benzyloxycarbonylaminopenicillanate,
1-methyl-1-(methoxycarbonyloxy)ethyl 6-benzyloxycarbonylaminopenicillanate and
1-methyl-1-(isopropoxycarbonyloxy)ethyl 6-benzyloxycarbonylaminopenicillanate,
respectively.

PREPARATION 6

Pivaloyloxymethyl 6-Benzyloxycarbonylaminopenicillanate 1,1-Dioxide

To 4.65 g. of pivaloyloxymethyl 6-benzyloxycarbonylpenicillanate in 15 ml. of dichloromethane is added 4.00 g. of 3-chloroperbenzoic acid at 0° C. The reaction mixture is stirred at 0° C. for 1 hour and then at 25° C. for 24 hours. The solid material is removed by filtration, and the filtrate is evaporated in vacuo. The residue is partitioned between ethyl acetate and water at pH 7.5 and the ethyl acetate layer is removed. The ethyl acetate layer is dried, and concentrated to dryness in vacuo to give the title compound.

PREPARATION 7

Oxidation of each of the 6-benzyloxycarbonylpenicillanic acid esters of Preparation 5 with 3-chloroperbenzoic acid, according to the procedure of Preparation 6, affords;
3-phthalidyl 6-benzyloxycarbonylaminopenicillanate 1,1-dioxide,
4-crotonolactonyl 6-benzyloxycarbonylaminopenicillanate 1,1-dioxide,
γ-butyrolacton-4-yl 6-benzyloxycarbonylaminopenicillanate 1,1-dioxide,
acetoxymethyl 6-benzyloxycarbonylaminopenicillanate 1,1-dioxide,
hexanoyloxymethyl 6-benzyloxycarbonylaminopenicillanate 1,1-dioxide,
1-(acetoxy)ethyl 6-benzyloxycarbonylaminopenicillanate 1,1-dioxide,
1-(isobutyryloxy)ethyl 6-benzyloxycarbonylaminopenicillanate 1,1-dioxide,
1-methyl-1-(acetoxy)ethyl 6-benzyloxycarbonylaminopenicillanate 1,1-dioxide,
1-methyl-1-(hexanoyloxy)ethyl 6-benzyloxycarbonylaminopenicillanate 1,1-dioxide,
methoxycarbonyloxymethyl 6-benzyloxycarbonylaminopenicillanate 1,1-dioxide,
propoxycarbonyloxymethyl 6-benzyloxycarbonylaminopenicillanate 1,1-dioxide,
1-(ethoxycarbonyloxy)ethyl 6-benzyloxycarbonylaminopenicillanate 1,1-dioxide,
1-(butoxycarbonyloxy)ethyl 6-benzyloxycarbonylaminopenicillanate 1,1-dioxide,
1-methyl-1-(methoxycarbonyloxy)ethyl 6-benzyloxycarbonylaminopenicillanate 1,1-dioxide and
1-methyl-1-(isopropoxycarbonyloxy)ethyl 6-benzyloxycarbonylaminopenicillanate,
respectively.

I claim:

1. A method of increasing the antibacterial effectiveness of a β-lactam antibiotic in a mammalian subject, which comprises co-administering with said β-lactam antibiotic, to said mammalian subject, a β-lactam antibiotic effectiveness increasing amount of a compound of the formula

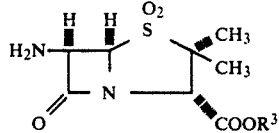

or a pharmaceutically-acceptable acid-addition salt thereof or a pharmaceutically-acceptable base salt thereof, wherein $R^3$ is selected from the group consisting of hydrogen, 3-phthalidyl, 4-crotonolactonyl, γ-butyrolacton-4-yl and groups of the formula

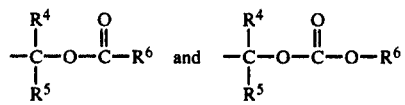

wherein $R^4$ and $R^5$ are each selected from the group consisting of hydrogen and alkyl having from 1 to 2 carbon atoms, and $R^6$ is alkyl having from 1 to 6 carbon atoms and wherein said β-lactam antibiotic is selected from the group consisting of
6-(2-phenylacetamido)penicillanic acid,
6-(2-phenoxyacetamido)penicillanic acid,
6-(2-phenylpropionamido)penicillanic acid,
6-(D-2-amino-2-phenylacetamido)penicillanic acid,
6-(D-2-amino-2-[4-hydroxyphenyl]acetamido)-penicillanic acid,
6-(D-2-[4-ethylpiperazin-2,3-dione-1-carboxamido]-2-phenylacetamido)penicillanic acid,
6-(D-2-[4-hydroxy-1,5-naphthyridine-3-carboxamido]-2-phenylacetamido)penicillanic acid,
6-(D-2-[imidazolidin-2-one-1-carboxamido]-2-phenyl-acetamido)penicillanic acid,
6-(D-[3-methylsulfonylimidazolidin-2-one-1-carboxamido]-2-phenylacetamido)penicillanic acid,
6-(D-2-[3-furfurylidineamino-2-oxoimidazolidine-1-carboxamido]-2-[4-hydroxyphenyl]acetamido)penicillanic acid,
7-(D-2-formyloxy-2-phenylacetamido)-3-([1-methyl-5-tetrazolyl]thiomethyl)-3-desacetoxymethylcephalosporanic acid,
7-(D-2-amino-2-[4-hydroxyphenyl]acetamido)-desacetoxycephalosporanic acid,
7-(2-[2-thienyl]acetamido)cephalosporanic acid,
7-(2-[1-tetrazolyl]acetamido-3-([5-methyl-1,3,4-thiadiazoly-2-yl]thiomethyl)-3-desacetoxymethylcephalosporanic acid,
7-(D-2-amino-2-phenylacetamido)desacetoxycephalosporanic acid,
7-(D-2-hydroxy-2-phenylacetamido)-3-([1-methyl-5-tetrazolyl]thiomethyl)-3-desacetoxymethylcephalosporanic acid,
7-(2-[4-pyridylthio]acetamido)cephalosporanic acid,
7-(D-2-amino-2-[1,4-cyclohexadienyl]acetamido)-cephalosporanic acid,
7-(D-2-[4-ethylpiperazin-2,3-dione-1-carboxamido]-2-[4-hydroxyphenyl]acetamido)-3-([1-methyl-5-tetrazolyl]thiomethyl)-3-desacetoxymethylcephalosporanic acid,
and the pharmaceutically-acceptable salts thereof.

2. The method according to claim 1 wherein $R^3$ is selected from the group consisting of hydrogen, alkanoyloxymethyl having from 3 to 7 carbon atoms, 1-(alkanoyloxy)ethyl having from 4 to 8 carbon atoms, 1-methyl-1-(alkanoyloxy)ethyl having from 5 to 9 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, 3-phthalidyl, 4-crotonolactonyl and gamma-butyrolacton-4-yl.

3. The method according to claim 1, wherein $R^3$ is hydrogen.

4. The method according to claim 1, wherein $R^3$ is pivaloyloxymethyl.

5. The method according to claim 1, wherein $R^3$ is 1-(ethoxycarbonyloxy)ethyl.

6. The method according to either claim 3, claim 4 or claim 5, wherein said β-lactam antibiotic is selected from the group consisting of 6-(2-phenylacetamido)penicillanic acid, 6-(D-2-amino-2-phenylacetamido)penicillanic acid and the pharmaceutically-acceptable salts thereof.

* * * * *

UNITED STATES PATENT AND TRADEMARK OFFICE
CERTIFICATE OF CORRECTION

PATENT NO. : 4,260,598
DATED : April 7, 1981
INVENTOR(S) : Wayne E. Barth

It is certified that error appears in the above–identified patent and that said Letters Patent are hereby corrected as shown below:

On the title page, under "FOREIGN PATENT DOCUMENTS," in the second entry, "2824539" should read --2824535--.

On the title page, under "OTHER PUBLICATIONS," in the fourth entry (fifth line), "1972" should read --1772--.

Signed and Sealed this

Fourteenth Day of July 1981

[SEAL]

Attest:

GERALD J. MOSSINGHOFF

Attesting Officer

Commissioner of Patents and Trademarks